United States Patent
Majumdar

(10) Patent No.: US 11,016,161 B2
(45) Date of Patent: May 25, 2021

(54) METHOD AND AN APPARATUS FOR RECONSTRUCTING MAGNETIC RESONANCE IMAGE

(71) Applicant: SAMSUNG ELECTRONICS CO., LTD., Suwon-si (KR)

(72) Inventor: Shantanu Majumdar, Bangalore (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/451,808

(22) Filed: Jun. 25, 2019

(65) Prior Publication Data

US 2019/0391222 A1 Dec. 26, 2019

(30) Foreign Application Priority Data

Jun. 25, 2018 (IN) .............................. 201841023648
May 27, 2019 (IN) .............................. 201841023648

(51) Int. Cl.
*G01R 33/561* (2006.01)
*G01R 33/48* (2006.01)
(Continued)

(52) U.S. Cl.
CPC ..... *G01R 33/5616* (2013.01); *G01R 33/4818* (2013.01); *G01R 33/56509* (2013.01);
(Continued)

(58) Field of Classification Search
CPC ............ G01R 33/5616; G01R 33/4818; G01R 33/56509; G01R 33/56554; G01R 33/36;
(Continued)

(56) References Cited

U.S. PATENT DOCUMENTS 4,965,521 A * 10/1990 Egloff .............. G01R 33/56518
324/312
6,341,179 B1 1/2002 Stoyle et al.
(Continued)

FOREIGN PATENT DOCUMENTS

EP 2858559 A0 1/2014
WO 02/46784 A2 6/2002
(Continued)

OTHER PUBLICATIONS

Dr. Jae-Moon Jo "Samsung to become leading medical equipment company" Market reports, Mar. 3, 2012, retrieved from [ http://www.healthcare-in-europe.com/en/article/9499-Samsung_to_become_leading_medical_equipment_company.html ] (3 pages total).
(Continued)

*Primary Examiner* — Gregory H Curran
(74) *Attorney, Agent, or Firm* — Sughrue Mion, PLLC

(57) ABSTRACT

Provided is an apparatus of reconstructing a magnetic resonance (MR) image, the apparatus including: a memory storing instructions; and at least one processor configured to execute the instructions to: obtain a plurality of segments of K-space data corresponding to a plurality of pulses which are applied to an object based on a pulse sequence; determine, based on radio frequency (RF) coils of the apparatus, a correction coefficient for merging the plurality of segments of K-space data; and generate a magnetic resonance (MR) image of the object by merging the plurality of segments of K-space data based on the determined correction coefficient.

18 Claims, 13 Drawing Sheets

(51) Int. Cl.
    *G01R 33/565* (2006.01)
    *G16H 30/20* (2018.01)
    *G01R 33/36* (2006.01)
    *G01R 33/385* (2006.01)
    *G06T 11/00* (2006.01)

(52) U.S. Cl.
    CPC ....... *G01R 33/56554* (2013.01); *G16H 30/20* (2018.01); *G01R 33/36* (2013.01); *G01R 33/385* (2013.01); *G06T 11/003* (2013.01); *G06T 2211/40* (2013.01)

(58) Field of Classification Search
    CPC . G01R 33/385; G06T 11/003; G06T 2211/40; G16H 30/20
    See application file for complete search history.

(56) References Cited

U.S. PATENT DOCUMENTS

| | | | |
|---|---|---|---|
| 2007/0085538 A1* | 4/2007 | Hinks | G01R 33/56341 324/309 |
| 2010/0164495 A1 | 7/2010 | Takizawa et al. | |
| 2015/0084629 A1 | 3/2015 | Porter | |
| 2015/0253408 A1 | 9/2015 | Grodzki et al. | |
| 2015/0323634 A1 | 11/2015 | Polimeni et al. | |
| 2017/0363703 A1 | 12/2017 | Arunachalam | |

FOREIGN PATENT DOCUMENTS

| | | |
|---|---|---|
| WO | 2012047771 | 4/2012 |
| WO | 2014004870 A1 | 1/2014 |

OTHER PUBLICATIONS

Siemens Healthineers "Resolve" retrieved on Jun. 24, 2019, retrieved from [ https://www.siemens-healthineers.com/en-us/magnetic-resonance-imaging/options-and-upgrades/clinical-applications/syngo-resolve/use ] (8 pages total).

Markets and Markets "Magnetic Resonance Imaging Systems Market by Architecture (Open MRI Systems and Closed MRI Systems (Standard Bore and Wide Bore)), Field Strength (Low-to-mid Field, High-field (1.5T and 3T), and Very-high Field)—Global Forecast to 2023" Market Reports, Apr. 2018, [retrieved from http://www.marketsandmarkets.com/Market-Reports/magnetic-resonance imaging-market-99.html ] (8 pages total).

Communication dated Oct. 7, 2019 issued by the International Searching Authority in counterpart Application No. PCT/KR2019/007682 (PCT/ISA/220, PCT/ISA/210, and PCT/ISA/237).

Communication dated Mar. 1, 2021 issued by the European Patent Office in application No. 19826105.9.

Uecker, M., et al., "Inverse Reconstruction Method for Segmented Multishot Diffusion-Weighted MRI With Multiple Coils", Magnetic Resonance in Medicine, vol. 62, No. 5, XP055222160, Nov. 1, 2009, pp. 1342-1348.

Holdsworth, S., et al., "Robust GRAPPA-Accelerated Diffusion-Weighted Readout-Segmented [RS]-EPI", Magnetic Resonance in Medicine, vol. 62, No. 6, Dec. 1, 2009, XP055388894, pp. 1629-1640.

Xu, Y., et al., "An iterative reconstruction technique for geometric distortion-corrected segmented echo-planar imaging", Magnetic Resonance Imaging, vol. 26, No. 10, Dec. 1, 2008, XP025671555, pp. 1406-1414.

* cited by examiner

Reduced FOV based RS-EPI

Sagittal　　　　　　Axial　　　　　　Coronal

METHOD AND AN APPARATUS FOR RECONSTRUCTING MAGNETIC RESONANCE IMAGE

CROSS-REFERENCE TO RELATED APPLICATION(S)

This application is based on and claims priority under 35 U.S.C. § 119 to an Indian application number 201841023648 filed on Jun. 25, 2018, in the Indian Patent Office, and of an Indian patent application number 201841023648 filed on May 27, 2019, in the Indian Patent Office, the disclosures of which are incorporated by reference herein in its entirety.

BACKGROUND

1. Field

The disclosure relates to a magnetic resonance imaging (MRI), in particular, a method and an apparatus for reconstructing a magnetic resonance (MR) image using readout-segmented echo-planar imaging (RS-EPI) data.

2. Description of the Related Art

Magnetic resonance imaging (MRI) is a known imaging modality to image internal organs (e.g. brain, knee, liver, heart, or the like) of a human body for clinical diagnosis of diseases. FIGS. 1A, 1B, 1C, and 1D illustrate example MR images of a knee, a brain, an abdomen, and a heart, respectively.

MRI system uses a combination of a high static magnetic field (B0) (e.g. 3 Tesla), spatially varying gradient magnetic field (G) and radiofrequency (RF) magnetic field pulses (B1) to generate the image data. Compared to X-rays using ionizing radiation, MRI is safe for a long scan time. MRI provides better contrast for soft tissues compared to other imaging modalities such as computed tomography (CT). Ultrahigh resolution (submillimeter) images may be obtained using MRI. An echo planar imaging (EPI) method may be used for functional MRI, and diffusion-weighted MRI, perfusion MRI, cardiac imaging, etc., for clinical applications such as detection and staging of ischemic stroke, Alzheimer's disease and cancerous tumors and in areas such as neuroimaging and musculoskeletal MRI. EPI is a high-speed image capturing technique capable of obtaining data by exciting a spin due to one RF pulse by rapidly vibrating a gradient magnetic field coil.

FIG. 2 illustrates an example scenario of construction of MR images using a readout-segmented echo-planar imaging (RS-EPI), according to a related art. MRI raw data or k-space data are acquired in 'segments' along a readout acquisition direction using an echo-planar imaging trajectory in RS-EPI. Using RS-EPI, high resolution (submillimeter) images may be obtained, which may improve the accuracy of clinical diagnosis. RS-EPI may be useful for reducing artifacts resulting from susceptibility and B0 inhomogeneity. RS-EPI may be used for diagnosis of stroke and dementia, tumor or the like.

FIG. 3 illustrates images constructed using single shot diffusion-weighted imaging (ssDWI) with EPI and RS-EPI, according to a related art. Two dimensional (2D) navigator signals may be used in the existing methods for correction of imaging artifacts induced by motion.

FIG. 4 is a flow diagram of an existing method for reconstructing an MR image, according to a related art. At 402, the method includes performing a navigator-selected Raw Data (k-space data) reacquisition. At 404, the method includes pre-processing corrections. At 406, the method includes performing segment merging via simple combination in the k-space. At 408, the method includes generating a DICOM image. The pre-processing corrections at 404 includes performing Nyquist ghost/phase correction at 404a, performing a parallel imaging reconstruction at 404b, and performing 2D navigator-based motion correction at 404c.

In the existing image reconstruction method, the segmented raw data (k-space data) are pre-processed for EPI Nyquist ghost correction, GeneRalized Autocalibrating Partial Parallel Acquisition (GRAPPA) reconstruction and motion correction. The corrected segment data are used to fill a full k-matrix. The readout data have overlap in k-space along readout direction in order to avoid gaps which are made after a phase correction is performed in the k-space of the full matrix.

SUMMARY

According to an embodiment of the disclosure, an apparatus of reconstructing a magnetic resonance (MR) image is provided. The apparatus includes: a memory storing instructions; and at least one processor configured to execute the instructions to: obtain a plurality of segments of K-space data corresponding to a plurality of pulses which are applied to an object based on a pulse sequence; determine, based on radio frequency (RF) coils of the apparatus, a correction coefficient for merging the plurality of segments of K-space data; and generate a magnetic resonance (MR) image of the object by merging the plurality of segments of K-space data based on the determined correction coefficient.

Accordingly, embodiments herein provide a method for performing an iterative MRI reconstruction of RS-EPI data. The method includes obtaining, by an image acquisition system, MRI K-space data based a segmented echo planar imaging procedure. Further, the method includes generating, by the image acquisition system, multiple segments of K-space data based on the MRI K-space data. Further, the method includes pre-processing, by the image reconstruction system, each segment of the K-space data. Further, the method includes generating, by the image reconstruction system, a complete K-space data by iteratively merging the pre-processed segments of the K-space data. Further, the method includes reconstructing, by the image reconstruction system, DICOM image via an inverse Fourier transform process applied on the complete K-Space data using a DICOM file generator.

In an embodiment, the segmented echo planar imaging procedure is a readout segmented echo planar imaging procedure.

In an embodiment, pre-processing, by the image reconstruction system, each segment of the K-space data includes performing an echo planar imaging (EPI) Nyquist ghost correction and parallel acquisition K-space data synthesis using multi-coil K-space data.

In an embodiment, the pre-processed each segment of the K-space data is iteratively merged by determining a phase correction data.

In an embodiment, the phase correction data is determined by minimizing image entropy during merging of each segments of the K-space data to form a complete K-space data.

In an embodiment, iteratively merging the pre-processed each segment of K-space data includes performing a K-space centre correction for the pre-processed each segment of the K-space data, performing a sum of K-space across the multi-coil data for each pre-processed segment, determining iteratively a correction coefficient value for the summed pre-processed each segment of the K-space data satisfying minimum image entropy criteria, and applying the correction coefficient value on the pre-processed each segment of multicoil K-space data to obtain corrected each segment of multicoil K-space data.

In an embodiment, the K-space centre correction for the pre-processed each segment of K-space data is performed by eliminating low frequency phase computed from the segment of K-space acquired in the center of the complete K-space.

Accordingly, embodiments herein provides an image reconstruction system for performing an iterative MRI reconstruction of RS-EPI data. The image reconstruction system includes MRI reconstruction engine coupled with a memory and a processor. The MRI reconstruction engine is configured to generate a complete K-space data by iteratively merging the pre-processed each segment of the K-space data acquired using readout-segmented echo planar imaging procedure. The MRI reconstruction engine is configured to construct DICOM image based on the complete K-Space data.

These and other aspects of embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of embodiments herein without departing from the spirit thereof, and embodiments herein include all such modifications.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1A:
FIGS. 1A, 1B, 1C, and 1D illustrate example MR images of internal organs, according to a related art.
Figure 1B:
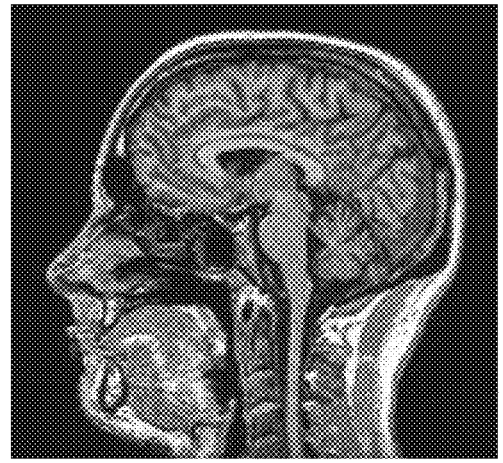
Figure 1C:
Figure 1D:
Figure 2:
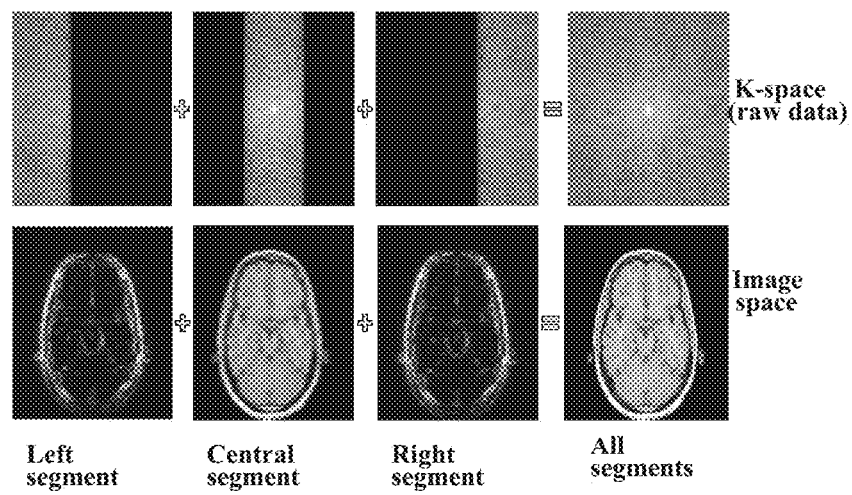
FIG. 2 illustrates an example scenario of construction of MR images using RS-EPI, according to a related art.
Figure 3:
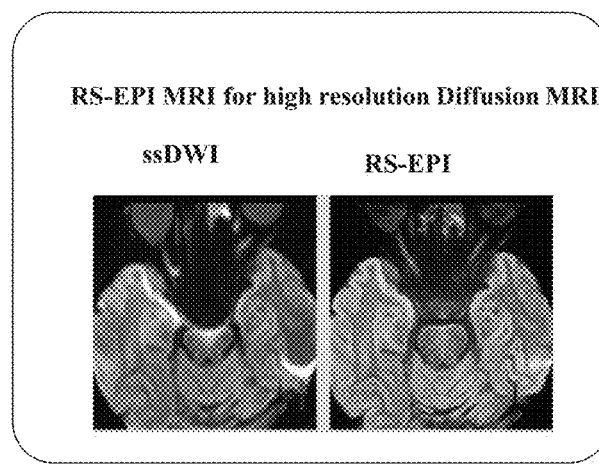
FIG. 3 illustrates images constructed using a single shot diffusion-weighted imaging (ssDWI) with EPI and RS-EPI, according to a related art.
Figure 4:
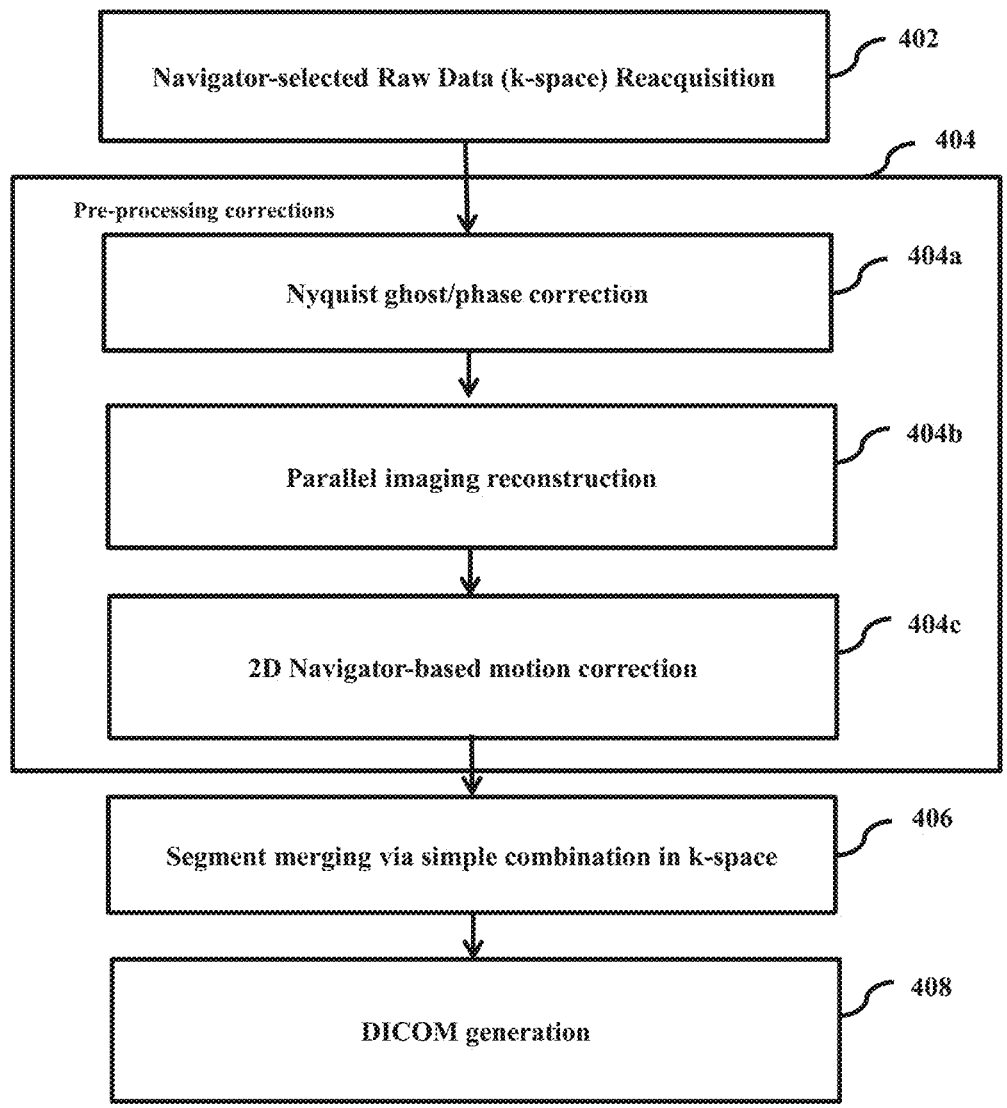
FIG. 4 is a flow diagram of an existing method for reconstructing an MR image, according to a related art.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein may be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

As used herein, the terms "1st" or "first" and "2nd" or "second" may use corresponding components regardless of importance or order and are used to distinguish one component from another without limiting the components.

The accompanying drawings are used to help easily understand various technical features and it should be understood that embodiments presented herein are not limited by the accompanying drawings. As such, the present disclosure should be construed to extend to any alterations, equivalents and substitutes in addition to those which are particularly set out in the accompanying drawings. Although the terms first, second, etc. may be used herein to describe various elements, these elements should not be limited by these terms. These terms are generally only used to distinguish one element from another.

Accordingly, embodiments herein provides a method for performing an iterative MRI reconstruction of RS-EPI data. The method obtaining, by an image acquisition system, MRI K-space data based on a segmented echo planar imaging procedure. Further, the method includes generating, by the image acquisition system, multiple segments of K-space data based on the MRI K-space data. Further, the method includes pre-processing, by the image reconstruction system, each segment of the K-space data. Further, the method includes generating, by the image reconstruction system, a complete K-space data by iteratively merging the pre-processed each segment of the K-space data. Further, the method includes reconstructing, by the image reconstruction system, digital imaging and communications in medicine (DICOM) image based on the complete K-Space data.

Unlike conventional methods and systems, the proposed method may include performing a fast iterative MR image reconstruction by combining multi-coil readout-segmented EPI data. In an embodiment, iterative reconstruction may be performed based on entropy minimization for readout segment merging of RS-EPI. In an embodiment, k-space centering correction may be performed using a triangular filter phase subtraction procedure. In an embodiment, a sum of coil data may be used to obtain a combined phase correction coefficient for segment merging. The phase correction coefficient may be applied to all coil data. In an embodiment, a segment overlap compensation filter may be used for performing the segment merging. In an embodiment, a three-segment data (K-space data) may be acquired and merged together to reduce chances of local minima issue and improve robustness of the convergence of the iterative algorithm. In an embodiment, coefficients may be applied by direct multiplication of phase correction coefficients with the multi coil segment data, and any further optimization in applying the coefficient may be not performed.

In an embodiment, the proposed method provides a fast merging with optimized merging of multi-coil (e.g. 32 coils) data. In an embodiment, the method provides an iterative merging using an entropy minimization procedure. According to an embodiment, the accuracy in k-space segment position may improve by a centering step because errors in a center of k-space resulting from phase variation are compensated by the centering step. In an embodiment, the method provides correction for artifacts affecting inter-segment alignment. In an embodiment, the method provides 2D phase correction.

The method may include performing a fast iterative MR image reconstruction by combining or merging segmented k-space data, such as, multi-coil readout-segmented EPI data. The method may utilize an entropy focus criterion as well as k-space center correction for the segmented k-space data acquisition. According to an embodiment, RS-EPI data acquisition procedure is performed without using a navigator pulse or a navigator image, thus, re-acquisition is not performed. In an embodiment, motion correction may be performed via the fast iterative segment merging (FISM) method. In the FISM method a fast iterative segment merging method may be used with k-space center correction during the reconstruction stage.

The method may be used in DWI, function MRI and clinical applications such as acute brain ischemic stroke, cancer detection and monitoring of therapy, early diagnosis of osteoarthritis in knee.

Figure 5:
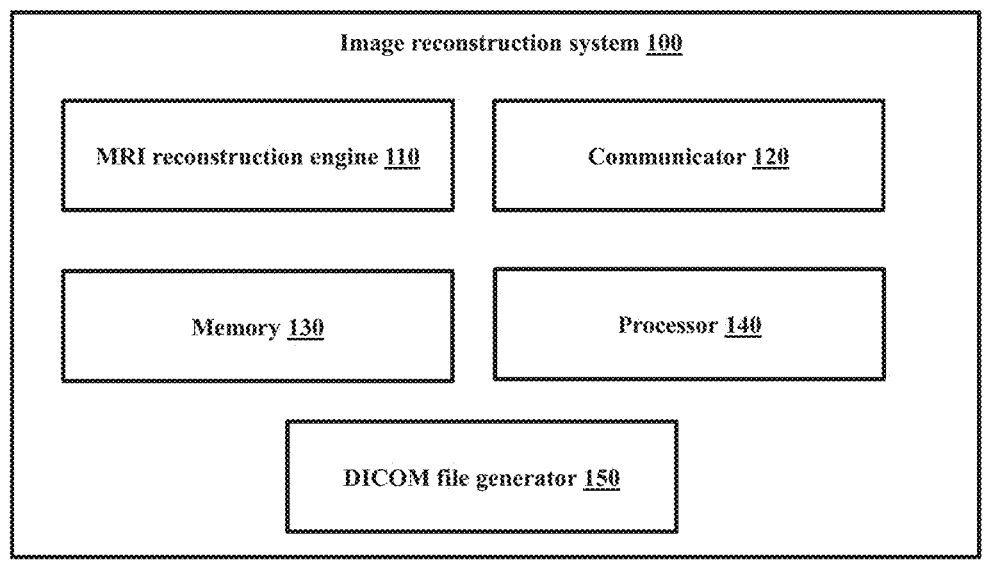
FIG. 5 is a block diagram of an image reconstruction system for performing an iterative MRI reconstruction for obtaining RS-EPI data, according to an embodiment.

FIG. 5 is a block diagram of an image reconstruction system 100 for performing an iterative MRI reconstruction for obtaining RS-EPI data, according to an embodiment. In an embodiment, the image reconstruction system 100 includes an MRI reconstruction engine 110, a communicator 120, a memory 130, a processor 140 and a DICOM file generator 150. The image reconstruction system may be an apparatus of reconstructing a magnetic resonance (MR) image.

Figure 8:
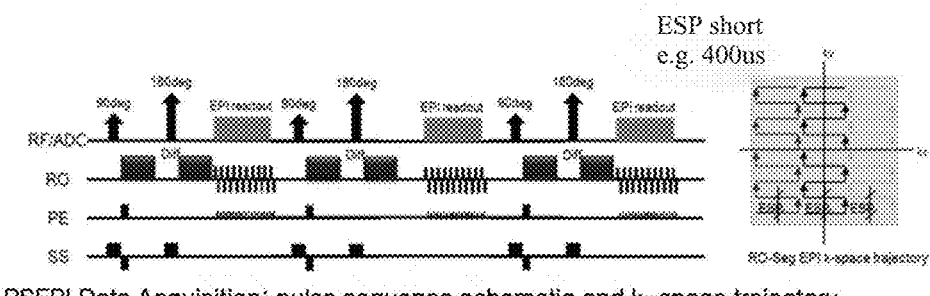
FIG. 8 illustrates an example pulse sequence diagram and an example k-space trajectory, according to an embodiment.

The processor 140 is coupled with the MRI reconstruction engine 110, the communicator 120, and the memory 130. The MRI reconstruction engine 110 is configured to process MRI K-space data based on a segmented echo planar imaging procedure. The MRI K-space data may be obtained, based on the segmented echo planar imaging procedure, as shown in the FIG. 8. FIG. 8 illustrates an example pulse sequence diagram (schematic) and an example k-space trajectory according to an embodiment. In an embodiment, the segmented echo planar imaging procedure is a readout segmented echo planar imaging procedure.

Based on the MRI K-space data, the MRI reconstruction engine 110 may pre-process multiple segments of K-space data acquired using readout-segmented echo planar imaging procedure. In an embodiment, the MRI reconstruction engine 110 may generate complete K-space data by iteratively merging the pre-processed each segment of K-space data. The MRI reconstruction engine 110 may generate a DICOM image based on the complete K-Space data using the DICOM file generator 150.

In an embodiment, each segment of K-space data is pre-processed by performing an EPI phase correction and synthesis of parallel K-space data acquisition based on multi-coil K-space data. In an embodiment, the pre-processed segments of the K-space data are iteratively merged based on determining phase correction data. The phase correction data may be determined by minimizing image entropy during merging of the segments of the K-space data to generate complete K-space data.

In an embodiment, pre-processed segments of K-space data are iteratively merged based on performing a K-space centre correction for the pre-processed segments of the K-space data, determining a sum of K-space data across the multi-coil data for each segment, determining iteratively a correction coefficient value for the summed pre-processed segments of the K-space data which satisfy a minimum image entropy criteria; and applying the correction coefficient value on the pre-processed segments of multicoil K-space data to obtain corrected segments of multicoil K-space data.

In an embodiment, the K-space centre correction for the pre-processed segments of K-space data is performed based on filtering or eliminating low frequency phase computed from a center segment of K-space acquired in the center of the complete K-space.

The processor 140 is configured to execute instructions stored in the memory 130 and to perform various processes. The communicator 120 is configured for communicating internally between internal hardware components and with external devices via one or more networks.

The memory 130 also stores instructions to be executed by the processor 140. The memory 130 may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the memory 130 may, in some examples, be considered a non-transitory storage medium. The term "non-transitory" may indicate that the storage medium is not embodied in a carrier wave or a propagated signal. However, the term "non-transitory" should not be interpreted that the memory 130 is non-movable. In some examples, the memory 130 may be configured to store larger amounts of information than the memory. In certain examples, a non-transitory storage medium may store data that can, over time, change (e.g., in Random Access Memory (RAM) or cache).

Other components of the image reconstruction system 100 may include a processor configured to execute instructions stored in a memory included in the other components or the memory of the image reconstructions system 100, in order to perform corresponding operations and functions.

Although the FIG. 5 shows various hardware components of the image reconstruction system 100 but it should be understood that embodiments are not limited thereto. In an embodiment, the image reconstruction system 100 may include less or more components than ones shown in FIG. 5. In an embodiment, the labels or names of the components are used only for illustrative purpose and does not limit the scope of the disclosure. One or more components may be combined together to perform same or substantially similar function to perform the iterative MRI reconstruction of RS-EPI data.

Figure 6:
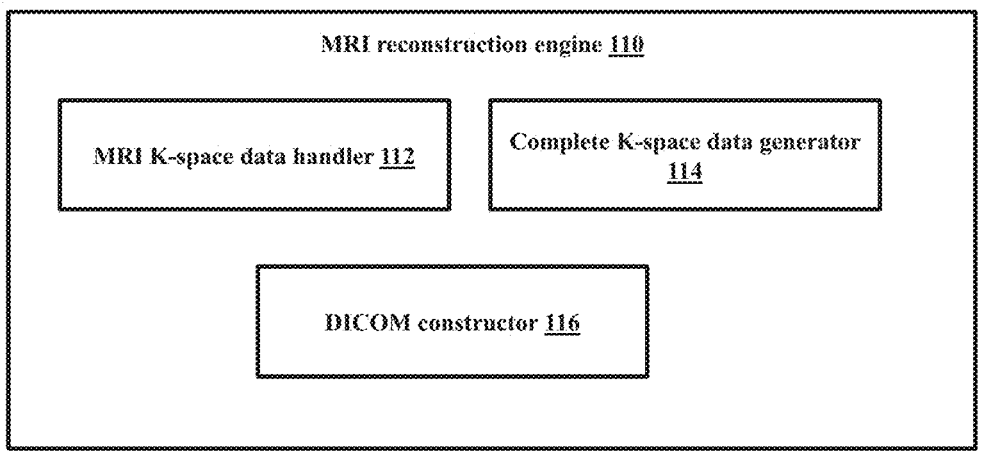
FIG. 6 is a block diagram of a MRI reconstruction engine, according to an embodiment.

FIG. 6 is a block diagram of the MRI reconstruction engine 110, according to an embodiment. In an embodiment, the MRI reconstruction engine 110 includes a MRI K-space data handler 112, a complete K-space data generator 114, and a DICOM constructor 116.

The MRI reconstruction engine 110 may be an apparatus of reconstructing a magnetic resonance (MR) image.

The MRI K-space data handler 112 may process MRI K-space data based on the segmented echo planar imaging procedure. Based on the MRI K-space data, the complete K-space data generator 114 may pre-process each segment of the K-space data. In an embodiment, the complete K-space data generator 114 may generate the complete K-space data by iteratively merging the pre-processed segments of the K-space data. The DICOM constructor 116 may construct the DICOM image based on the complete K-Space data.

In an embodiment, the MRI K-space data generator 114 may perform the k-space center correction for multi-coil data. For each image slice, there may exist readout segments of the k-space matrix, and for each segment there may exist multi-coil data. In an embodiment, each segment coil data are inverse-Fourier-transformed to image domain. The k-space data for central readout segment which corresponds to the center of k-space is multiplied with a triangular low pass filter and inverse-Fourier-transformed to image domain. Then, the phase of the central segment coil data may be subtracted from the phase of the segment coil data, which is conducted for each coil. Next, the data are forward-Fourier-transformed to k-space.

In order to speed up the segment merging in FISM and improve accuracy of segment merging, the center correction is performed. This step ensures that the central segment of all the multi-coil k-space data are aligned and matched. Similar phase subtraction is conducted to off-center segments to ensure consistent operation on these off-center segments.

The complete K-space data generator 114 may perform the coefficient calculation for segment merging. The segment data alignment in k-space from center correction enables the complete K-space data generator 114 to perform the coefficient calculation for segment merging jointly on the sum of multi-coil data instead of coil-wise iterative merging. The k-space data from all coils are summed and a set of sum-k-space data for the segments is determined. In an embodiment, a set of three readout segments of k-space data is collected, and the central segment may be always selected as one of the set of three readout segments of k-space data. Segments of k-space data are merged to generate a completed k-space data of three segments, by using an iterative algorithm that minimizes the image entropy (called as the entropy focus criterion) at every step of the iteration of merging. During the iteration of merging, an overlap compensating filter may be applied to each segment data to ensure that the segment overlap from each consecutive segments are linearly interpolated and then merged. The overlap compensating filter may prevent the formation of spurious peaks at the overlapped region. In an embodiment, the coefficients for the zeroth and first order phase correction may be computed and applied to the k-space segments in order to satisfy the entropy focus criterion. Once the coefficients are stored after the first iteration, in the next second iteration, two more segment data are collected and merged with the output of the previous iteration to compute the phase correction coefficients for this second iteration. The iteration of calculation of correction coefficient and merging of segments of k-space data continues till all segments are processed (summed) and coefficients are calculated.

The complete K-space data generator 114 may apply the phase correction using the calculated coefficients to all segments of k-space data. In an embodiment, the coefficients are calculated from a sum of coil data in k-space data, and may be applied to each coil data separately since the coil data are aligned from center correction in the first sub-module. In an embodiment, the segments are multiplied with the corresponding phase correction coefficients calculated from the iterative segment merging using the entropy focus criterion, then multiplied with the overlap compensating filter and then merged to create the complete k-space.

After completion of the iteration of of calculation of correction coefficient and merging of segments of k-space data, the complete k-space data may be generated for the rest of the image reconstruction pipeline including performing partial Fourier filling of k-space (if this option is used) and DICOM image generation for display and storage.

Although the FIG. 6 shows various hardware components of the MRI reconstruction engine 110 but it should be understood that embodiments are not limited thereto. In other embodiments, the MRI reconstruction engine 110 may include less or more components than ones shown in FIG. 6. In an embodiment, the labels or names of the components are used only for illustrative purpose and does not limit the scope of the disclosure. One or more components may be combined together to perform same or substantially similar function to perform the iterative MRI reconstruction for obtaining RS-EPI data.

Figure 7:
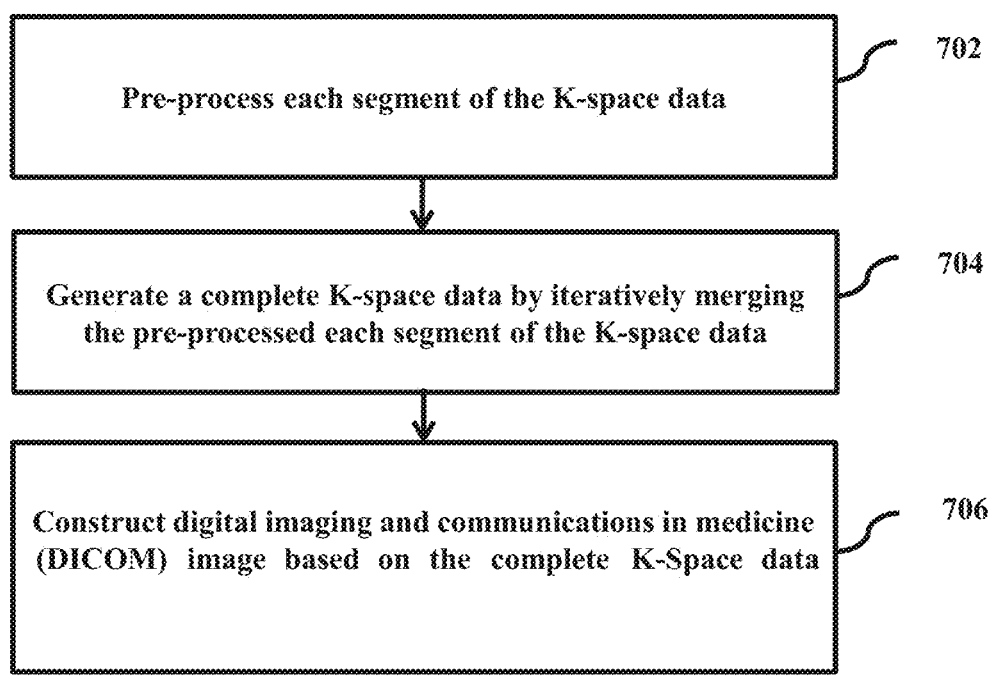
FIG. 7 is a flow diagram of a method for performing iterative MRI reconstruction of RS-EPI data, according to an embodiment.

FIG. 7 is a flow diagram of a method for performing the iterative MRI reconstruction of RS-EPI data, according to an embodiment. The operations (702-706) may be performed by the MRI reconstruction engine 110, but are not limited thereto. For example, the operations at 702-706 or other operations explained herein may be performed by at least one processor of an MRI apparatus. At 702, the method may include pre-processing each segment of the K-space data. At 704, the method may include generating the complete K-space data by iteratively merging the pre-processed each segment of the K-space data. At 706, the method may include constructing digital imaging and communications in medicine (DICOM) image based on the complete K-Space data.

The various actions, acts, blocks, steps, or the like in the flow diagram of FIG. 7 may be performed in the order presented, in a different order or simultaneously. In an embodiment, in some embodiments, some of the actions, acts, blocks, steps, or the like may be omitted, added, modified, skipped, or the like without departing from the scope of the disclosure.

Figure 9:
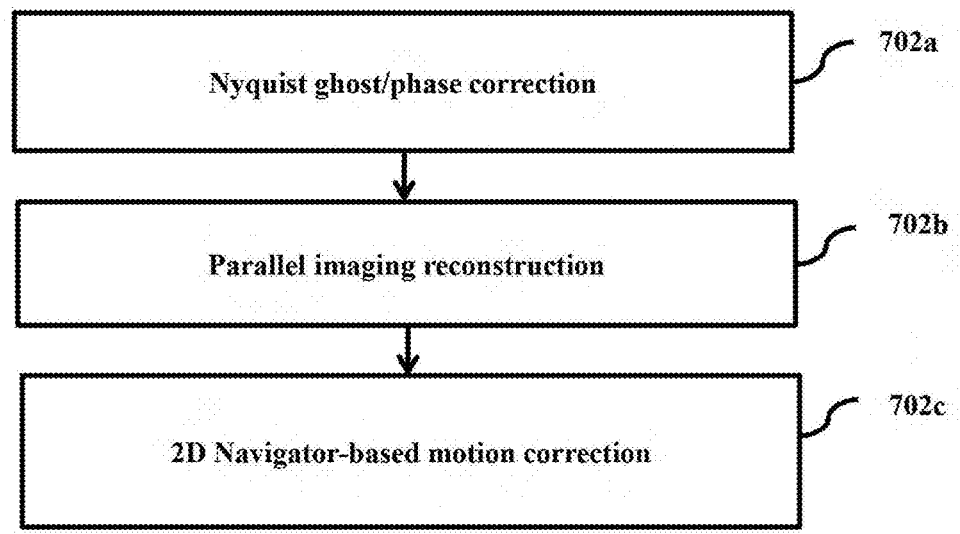
FIG. 9 is a flow chart illustrating various operations for pre-processing each segment of K-space data, according to an embodiment.

FIG. 8 illustrates an example pulse sequence diagram (schematic) and an example k-space trajectory according to an embodiment. The number of lines per a segment of K-space data is the same with another segment of K-space data. In an embodiment, the segmented echo planar imaging procedure may be a readout segmented echo planar imaging procedure. In an embodiment, segments of k-space data may include a left, center, and right segments of k-space data as shown as FIG. 8. According to an embodiment, k-space data may be obtained by sampling MR signal emitted from the target object. In this regard, the k-space data refers to a signal generated by arranging an MR signal in a k-space, wherein the MR signal is an RF signal received from each of channel coils included in a high-frequency multi-coil. The k-space may refer to a group of a plurality of pieces of k-space data with which an image corresponding to each slice is generated. When the high-frequency multi-coil includes n channel coils, each of the n channel coils may individually receive an MR signal. N pieces of k-space data that correspond to the n channel coils, respectively, may be obtained by using MR signals received from the n channel coils, respectively. FIG. 9 is a flow chart illustrating various operations for pre-processing each segment of K-space data, according to an embodiment. The operations (702a-702c) are performed by the MRI reconstruction engine 110.

At 702a, the method may include performing a Nyquist ghost/phase correction. At 702b, the method may include performing parallel imaging reconstruction. At 702c, the method may include performing 2D navigator-based motion correction.

The various actions, acts, blocks, steps, or the like in the flow diagram of FIG. 9 may be performed in the order presented, in a different order or simultaneously. In an embodiment, in some embodiments, some of the actions, acts, blocks, steps, or the like may be omitted, added, modified, skipped, or the like without departing from the scope of the disclosure.

Figure 10A:
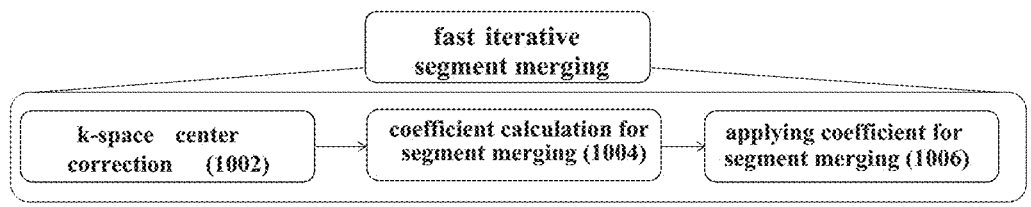
FIGS. 10A, 10B, and 10C are flow diagrams illustrating various operations for iteratively merging segments of K-space data, according to an embodiment.
Figure 10B:
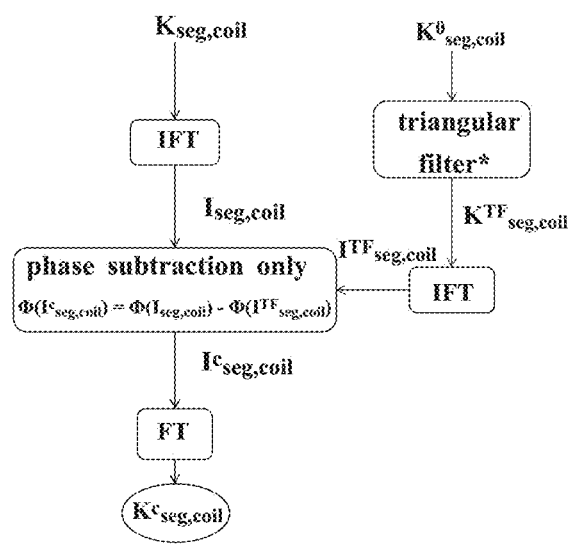
Figure 10C:
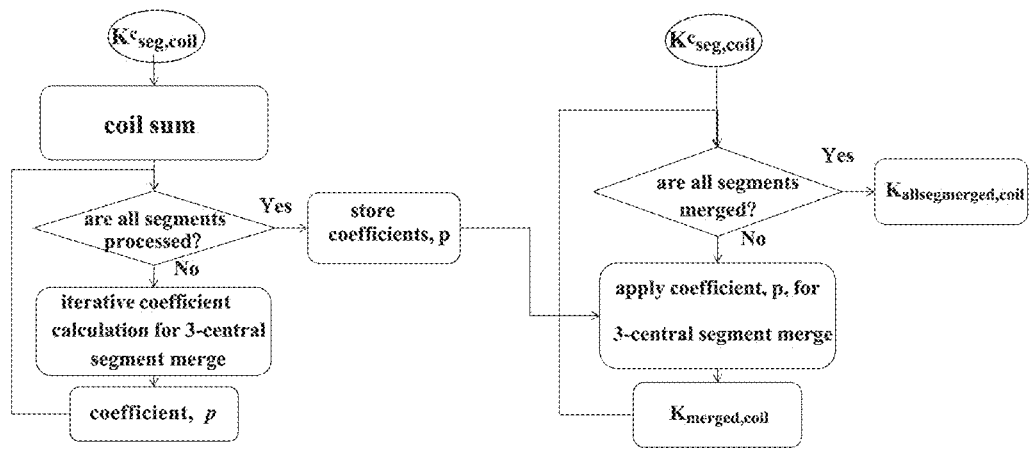

FIGS. 10A, 10B, and 10C are flow diagrams illustrating various operations for iteratively merging segments of K-space data, according to an embodiment.

Referring to FIG. 10A, fast iterative segment merging (FISM) may be performed by k-space center correction at 1002, coefficient calculation for segment merging at 1004, and applying a coefficient for segment merging at 1006.

Explanation of k-space center correction at 1002 is described by referring to FIG. 10B. Explanation of coefficient calculation for segment merging at 1004, and applying a coefficient for segment merging at 1006 is described by referring to FIG. 10C.

In RS-EPI, segmented data acquired using the RS-EPI pulse sequence is reconstructed using a series of reconstruction procedures. The key component of the image reconstruction for the RS-EPI is the merging of the k-space segments to obtain the complete k-space which is then subsequently used to generate the MR image. The method may be used to image reconstruction which may be used for RS-EPI imaging. The method is a fast iterative method for combining multi-coil readout-segmented EPI (RS-EPI) data for MR image reconstruction. The image reconstruction system 100 (i.e., Fast Iterative Segment merging (FISM) system) consists of three parts (i.e., K-space center correction part, coefficient calculation part for segment merging, and coefficient applying part for segment merging)

K-space center correction: At 1002 of FIG. 10B, the MRI K-space data generator 114 may perform the k-space center correction of multi-coil data. For each image slice, there may exist readout segments of the k-space matrix, and for each segment there may exist multi-coil data. Each segment coil data are inverse-Fourier-transformed to image domain. The k-space data for central readout segment, ($K^0_{seg,coil}$), which corresponds to the center of k-space is multiplied with the triangular low pass filter and inverse-Fourier-transformed to low frequency image domain. Then, the phase of the central segment coil data may be subtracted from the phase of the segment coil data, which is conducted for each coil. Next, the data are forward-Fourier-transformed to k-space as expressed as $K^c_{seg,coil}$.

The K-space center correction may be conducted to eliminate any center of k-space offset or error in the multi-coil segmented k-space RS-EPI data, which may result in segment mismatch during merging if not they are corrected. The forward and inverse Fourier transforms may be defined below as:

$$K(k, l) = \frac{1}{\sqrt{MN}} \sum_{m=0}^{M-1} \sum_{n=0}^{N-1} I(m, n) e^{-i2\pi\left(\frac{mk}{M} + \frac{nl}{N}\right)}$$

$$I(m, n) = \frac{1}{\sqrt{MN}} \sum_{k=0}^{M-1} \sum_{l=0}^{N-1} K(k, l) e^{i2\pi\left(\frac{mk}{M} + \frac{nl}{N}\right)}$$

Here, the first equation shows the forward-Fourier-transform (k-space) for the image given as I(m,n) and the second equation shows the inverse Fourier transform (image) for the given k-space K(k,l). k,l are k-space axis variables and m,n are image space axis variables. M, N are size of the image or k-space matrix such that $0 \le k,m \le M-1$ and $0 \le l,n \le N-1$.

Coefficient calculation part for segment merging: In an embodiment, iterative merging using entropy minimization algorithm may be applied to the sum of all coil data to estimate the coefficients for segment merging. Since k-space center correction is conducted in the K-space center correction, sum of all coil data may be used, instead of using data of individual coils separately. According to an embodiment, the segment merging process may speed up by order of number of coils (~about 32 times for a head coil, ~about 18 times for a knee coil).

Merge coefficient calculation (p coefficient) using iterative method: The method may be used to estimates the phase correction terms by minimizing image entropy from the correctly merged segments. The p coefficient is represented as equation (1):

$$p_{corr} = \arg\left(\min_p E(I(k_p))\right) \tag{1}$$

where $p = p_{lx0}, p_{lx1}, p_{ly0}, p_{ly1}, p_{rx0}, p_{rx1}, p_{ry0}, p_{ry1}$
where, image entropy is defined as equation (2):

$$E(I) = -\sum_{i,j} \frac{I_{ij}}{I_{max}} \log\left(\frac{I_{ij}}{I_{max}}\right) \tag{2}$$

A correction model for k-space data is represented as equation $$k_p = k_l e^{-j\varphi_{lp}} + k_c + k_r e^{-\varphi_{rp}} \tag{3}$$

where, $\varphi_{lp} = (p_{ly0} + p_{ly1}y)^*(p_{lx0} + p_{lx1}x)$, and $\varphi_{rp} = (p_{ry0} + p_{ry1}y)^*(p_{rx0} + p_{rx1}x)$ (4)

$k_l$, $k_c$ and $k_r$ are left, center and right segments of raw (measured) k-space data, respectively.

Coefficient applying part for segment merging: Coefficients calculated from the coefficient calculation for segment merging are then applied to each coil data. This step may involve only multiplication of coefficients to coil data and, thus, the time is saved to generate an MR image.

At 1004 and At 1006 of FIG. 10C, the complete K-space data generator 114 may perform the coefficient calculation for segment merging. The segment data alignment in k-space from center correction may facilitate performing coefficient calculation for segment merging jointly on the sum of multi-coil data instead of coil-wise iterative merging. The k-space data from all coils are summed and a set of sum-k-space data for the segments may be determined as below equation (5)

$$K_{seg}^c = \sum_{coil} K_{seg,coil}^c \qquad (5)$$

In an embodiment, a set of three readout segments of k-space are collected, and the central segment may be always selected as one of the selections. Segments of k-space data are merged for the completed k-space of three segments k-space data, by using the iterative procedure that minimizes the image entropy (called as the entropy focus criterion) at every step of the iteration procedure of merging segments or calculating correction coefficients. During the iteration procedure, an overlap compensating filter may be applied to each segment data to ensure that the segment overlap from consecutive segments are linearly interpolated and then merged. The overlap compensating filter may prevent the formation of spurious peaks at the overlapped region. In an embodiment, the coefficients for the zeroth and first order phase correction may be applied to the k-space segments in order to satisfy the entropy focus criterion. After the coefficients are stored, in the next iteration, two more segment data are collected and merged with the output of the previous iteration to compute the phase correction coefficients for this iteration. The iteration of calculation of correction coefficient and merging of segments of k-space data continues till all segments are processed (summed) and coefficients are calculated.

The complete K-space data generator 114 may apply the phase correction using the calculated coefficients to all segment data. In an embodiment, coefficients are calculated from a sum of coil data in k-space data, and may be applied to each coil data separately since the coil data are aligned from center correction in the first sub-module. In an embodiment, segments are multiplied with the corresponding phase correction coefficients determined or calculated from the iterative segment merging using the entropy focus criterion, then multiplied with the overlap compensating filter and then merged to create the complete k-space.

Figure 11:
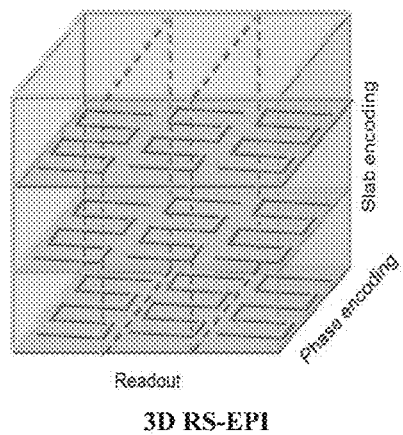
FIG. 11, FIG. 12, and FIG. 13 illustrate example scenarios in which RS-EPI is used for various applications, according to an embodiment.
Figure 12:
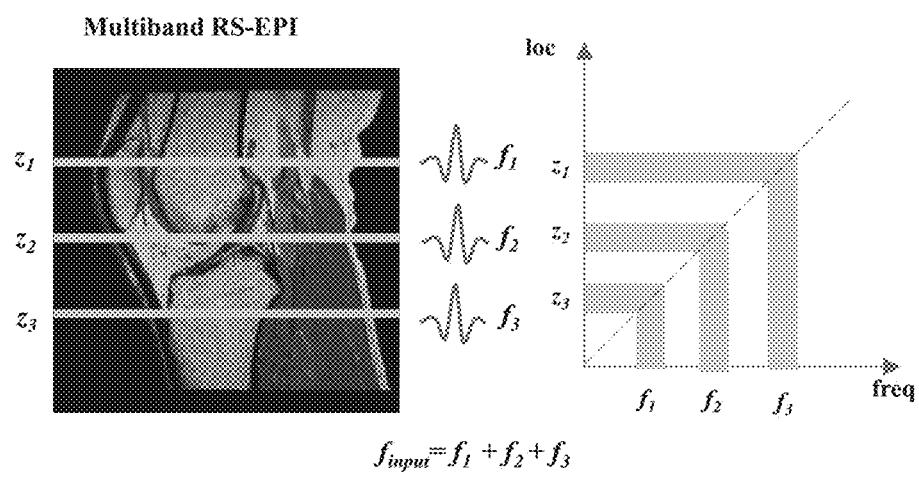
Figure 13:
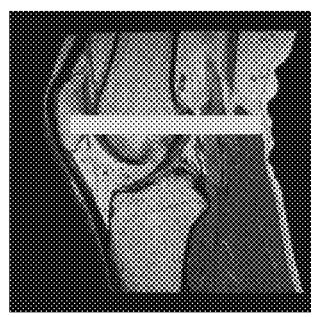
Figure 13:
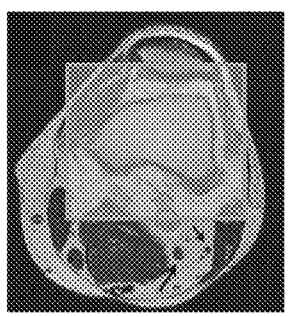
Figure 13:
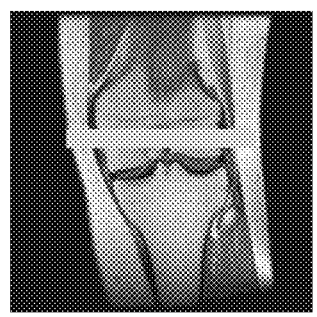

FIG. 11, FIG. 12, and FIG. 13 illustrate example scenarios in which RS-EPI is used for various applications, according to an embodiment.

As shown in the FIG. 11, the RS-EPI data may be used to perform 3D readout-segmented DWI so as to improve a signal-to-noise ratio of the received signal. As shown in the FIG. 12, the RS-EPI data may be used for segmented and multi-banded EPI for simultaneous multiple slice data acquisition for fast multivolume MRI scan. As shown in the FIG. 13, the RS-EPI data may be used with a reduced FOV method to achieve ultra-high image in-plane resolution (<0.25 mm$^2$).

In an embodiment, the RS-EPI data may be used for DWI application for high resolution knee cartilage imaging. This could be for clinical application of early diagnosis of osteoarthritis or used as a screening test for cartilage degradation. In another embodiment, the RS-EPI data may be used for DWI application for high resolution musculoskeletal (MSK) imaging. This could be for clinical application of diagnosis for bone marrow lesion and tumor. In another embodiment, the RS-EPI data may be used for DWI application for high resolution brain imaging. This could be for clinical application of diagnosis of acute ischemic stroke.

Figure 14:
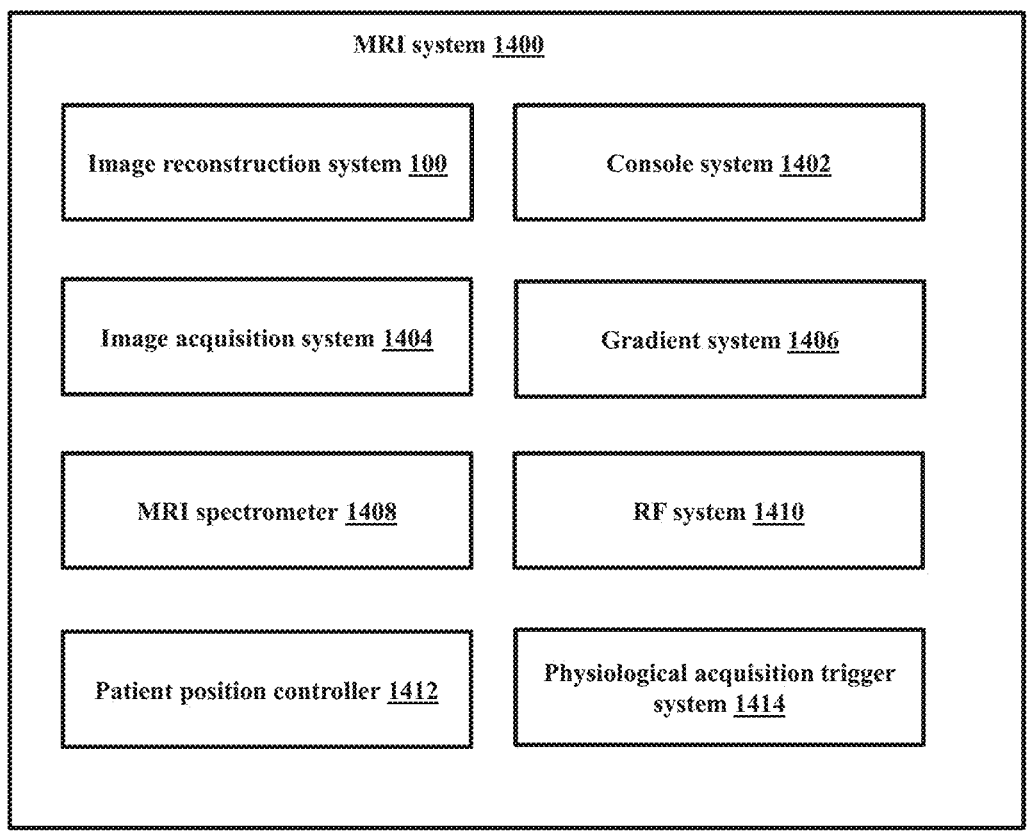
FIG. 14 is a schematic diagram illustrating a MRI system, according to an embodiment.

FIG. 14 is a schematic diagram illustrating a MRI system 1400, according to an embodiment. In an embodiment, the MRI system 1400 includes an image reconstruction system 100, a console system 1402, an image acquisition system 1404, a gradient system 1406, a MRI spectrometer 1408, a RF system 1410, a patient position controller 1412 and a physiological acquisition trigger system 1414. The MRI system 1400 may be an apparatus of reconstructing a magnetic resonance (MR) image.

The console system 1402 may communicate with the image reconstruction system 100, the image acquisition system 1404, the gradient system 1406, the MRI spectrometer 1408, the RF system 1410, the patient position controller 1412 the physiological acquisition trigger system 1414 and the image acquisition system 1416.

The operations and functions of the image reconstruction system 100 are explained above in conjunction with the FIG. 5 and FIG. 6.

The image acquisition system 1416 may acquire MRI K-space data based on a segmented echo planar imaging procedure. The image acquisition system 1416 may generate multiple segments of K-space data based on the MRI K-space data. The image reconstruction system 100 may a series of reconstruction pipeline processing which is used to reconstruct MR images from the MRI raw data. The RS-EPI raw data are pre-processed for Nyquist ghosting correction, parallel imaging reconstruction and navigator correction. The key component of RS-EPI reconstruction is the segment merging module which is executed after pre-processing.

After merging segments, the complete k-space data may be obtained to generate DICOM images. This is the system of interest since in segmented MRI data merging, the method that merges the raw data is a critical component of the reconstruction pipeline and determines the eventual image quality and clinical diagnostic value of the image. The system may be used to improve the image quality. The raw MRI k-space readout segment data are pre-processed for ghosting correction, parallel imaging reconstruction and navigator correction. The pre-processed readout segments are then merged or combined to create the complete k-space matrix which contains all the data corresponding to the prescribed image resolution.

In the image reconstruction system 100, the raw k-space data in MRI is in a Fourier domain and is not directly readable. The MR images are reconstructed from the raw data by using a series of MR image reconstruction pipeline processing. The console system 1402 provides the UI controls of the MRI scanner and its various operations. The image acquisition system 1404 is used to program the image raw data acquisition and performs operations of switching of the RF system 1410 and the gradient system 1406 to create MRI contrast (T1, T2, and Diffusion) and setting of the image resolution. The image acquisition system 1404 is also called as a pulse sequence system.

In the gradient system 1406, the magnetic field gradient created using the gradient coils is used to spatially localize the MR signals along three spatial axes which creates the MR images. The gradient system 1406 consists of gradient coils, amplifier and cooling systems.

In an embodiment, the MRI spectrometer 1408 provides a very high magnetic field (1.5 T, 3 T etc.) which polarizes the protons (H+) in scanned tissues and creates the magnetic resonance state required for the imaging. The MRI spectrometer 1408 houses the gradient and RF transmitter coils in a cylindrical co-axial setting. In the RF system 1410, the RF energy is transmitted and the MRI signal is received by the RF system 1410. The RF system 1410 may include transmit and receive RF coils, RF amplifiers and hardware filters.

In an embodiment, the patient position system 1412 controls the patient position with respect to MRI spectrometer 1408. In an embodiment, the physiological acquisition triggering system 1414 is used to trigger or gate data acquisition to synchronize with cardiac or respiratory signals.

Figure 15:
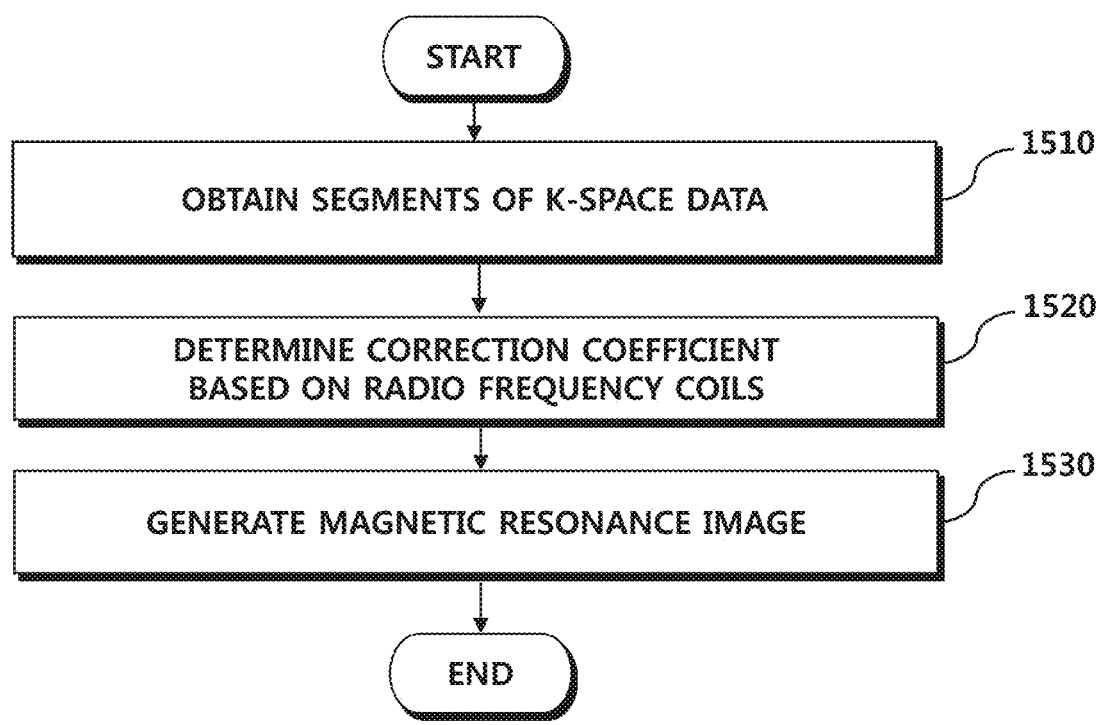
FIG. 15 is a flowchart of a method of reconstructing an MR image according to an embodiment.

FIG. 15 is a flowchart of a method of reconstructing an MR image according to an embodiment.

At 1510, segments of k-space data may be obtained. The segments of K-space data may correspond to a radio frequency (RF) pulses. The RF pulses are applied to an object, such as, a patient, based on a pulse sequence. In an embodiment, the pulse sequence may be readout-segmented echo-planar imaging (RS-EPI) pulse sequence. The pulse sequence may be a multi-shot pulse sequence.

In an embodiment, the segments of k-space data may be pre-processed. The pre-processing of the segments of k-space data is explained above.

At 1520, a correction coefficient may be determined based on RF coils. The RF coils may be multi-channel coils, and the correction coefficient is used for merging the segments of k-space data.

According to an embodiment, the correction coefficient may be determined iteratively based on the RF coils as explained above. For example, a first correction coefficient for a first RF coil may be determined, and then a second correction coefficient for a second RF coil may be determined based on the first correction coefficient. A third correction coefficient, . . . nth correction coefficient may be determined based on the second, . . . n−1th correction coefficient. The determined correction coefficient may the nth correction coefficient.

At 1530, a magnetic resonance (MR) image may be generated. In an embodiment, the MR image may be generated by merging the segments of k-space data. The merging of the segments may be based on the determined correction coefficient, such as, the nth correction coefficient.

In an embodiment, the segments of k-space data may be merged iteratively. The iterative merging is explained above. In an embodiment, the merging of the segments of K-space data and the calculation of the correction coefficient may be performed as a number of merged segments increasing. That is, the iteration of calculation of correction coefficient and merging of segments of k-space data continues till all segments are processed (summed) and coefficients are calculated.

When the segments of k-space data are merged, a navigator image is not used for correction according to an embodiment, because FISM is used instead.

Embodiments disclosed herein may be implemented using at least one software program running on at least one hardware device and performing network management functions to control the elements.

The foregoing description of the specific embodiments will so fully reveal the general nature of embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while embodiments herein have been described in terms of preferred embodiments, those skilled in the art will recognize that embodiments herein may be practiced with modification within the spirit and scope of embodiments as described herein.

What is claimed is:

1. An apparatus of reconstructing a magnetic resonance (MR) image, the apparatus comprising:
   a memory storing instructions; and
   at least one processor configured to execute the instructions to:
   obtain a plurality of segments of K-space data corresponding to a plurality of pulses which are applied to an object based on a pulse sequence;
   determine, based on radio frequency (RF) coils of the apparatus, a correction coefficient for merging the plurality of segments of K-space data; and
   generate a magnetic resonance (MR) image of the object by merging the plurality of segments of K-space data based on the determined correction coefficient,
   wherein the correction coefficient is determined based on a first correction coefficient for a first RF coil and a second correction coefficient for a second RF coil, and the second correction coefficient is determined based on the first correction coefficient.

2. The apparatus of claim 1, wherein the correction coefficient is determined iteratively based on the RF coils.

3. The apparatus of claim 1, wherein the at least one processor is further configured to execute the instructions to generate the MR image of the object by iteratively merging the plurality of segments of K-space data based on the determined correction coefficient.

4. The apparatus of claim 1, wherein the merging the plurality of segments of K-space data and the determining the correction coefficient for merging the plurality of segments of K-space data are performed as a number of merged segments increasing.

5. The apparatus of claim 1, wherein the plurality of segments of K-space data are merged without using a navigator image.

6. The apparatus of claim 1, wherein the plurality of segments of K-space data comprise a left, a center, and a right segments of K-space data.

7. The apparatus of claim 1, wherein the plurality of segments of K-space data are merged based on a phase subtraction with respect to a center segment of K-space data.

8. The apparatus of claim 1, wherein a number of lines per a segment of K-space data is the same with another segment of K-space data.

9. The apparatus of claim 1, wherein the at least one processor is further configured to execute the instructions to pre-process the plurality of segments of K-space data for phase correction.

10. The apparatus of claim 1, wherein the at least one processor is further configured to execute the instructions to pre-process the plurality of segments of K-space data by performing an echo planar imaging (EP) Nyquist ghost correction and performing parallel acquisition of the K-space data.

11. The apparatus of claim 1, wherein the pulse sequence comprises a multi-shot pulse sequence.

12. The apparatus of claim 1, wherein the pulse sequence comprises readout-segmented echo-planar imaging (RS-EPI) pulse sequence.

13. A method of reconstructing a magnetic resonance (MR) image, the method comprising:
   obtaining a plurality of segments of K-space data corresponding to a plurality of pulses which are applied to an object based on a pulse sequence;
   determining, based on radio frequency (RF) coils of the apparatus, a correction coefficient for merging the plurality of segments of K-space data; and
   generating a magnetic resonance (MR) image of the object by merging the plurality of segments of K-space data based on the determined correction coefficient,
   wherein the correction coefficient is determined based on a first correction coefficient for a first RF coil and a second correction coefficient for a second RF coil, and the second correction coefficient is determined based on the first correction coefficient.

14. The method of claim 13, wherein the correction coefficient is determined iteratively based on the RF coils.

15. The method of claim 13, wherein the generating the MR image comprises generating the MR image of the object by iteratively merging the plurality of segments of K-space data based on the determined correction coefficient.

16. The method of claim 13, wherein the merging the plurality of segments of K-space data and the determining the correction coefficient for merging the plurality of segments of K-space data are performed alternatively as a number of merged segments increasing.

17. The method of claim 13, wherein the plurality of segments of K-space data are merged without using a navigator image.

18. A computer program product comprising a computer readable medium comprising instructions which, when executed by at least one processor, cause the at least one processor to:
   obtain a plurality of segments of K-space data corresponding to a plurality of pulses which are applied to an object based on a pulse sequence;
   determine, based on radio frequency (RF) coils of the apparatus, a correction coefficient for merging the plurality of segments of K-space data; and
   generate a magnetic resonance (MR) image of the object by merging the plurality of segments of K-space data based on the determined correction coefficient,
   wherein the correction coefficient is determined based on a first correction coefficient for a first RF coil and a second correction coefficient for a second RF coil, and the second correction coefficient is determined based on the first correction coefficient.

* * * * *